United States Patent [19]

Badamchian et al.

[11] Patent Number: 5,705,486
[45] Date of Patent: Jan. 6, 1998

[54] ISOLATION OF NOVEL PEPTIDES FROM GREEN BARLEY LEAF EXTRACT AND USE SAME TO INHIBIT HUMAN PLATELET AGGREGATION

[75] Inventors: Mahnaz Badamchian, Herndon, Va.; Yoshihide Hagiwara, Rm. 1027, Osaka-Ekimae, The 3rd Bldg., 1-3 Umeda 1-chome, Kita-ku, Osaka; Hideaki Hagiwara, Kasai, both of Japan

[73] Assignee: Yoshihide Hagiwara, Osaka, Japan

[21] Appl. No.: 615,888

[22] Filed: Mar. 14, 1996

[51] Int. Cl.$^6$ ................................................ A61K 38/00
[52] U.S. Cl. ................................................ 514/17; 530/330
[58] Field of Search ................................ 530/330; 514/17

[56] References Cited

U.S. PATENT DOCUMENTS 4,943,562  7/1990  Jolles et al. ........................ 514/18

*Primary Examiner*—Cecilia J. Tsang
*Assistant Examiner*—C. Delacroix-Muirheid
*Attorney, Agent, or Firm*—Sherman and Shalloway

[57] ABSTRACT

Two penta-peptides, Asp-Asp-Asn-Asp-Asn and Asp-Asp-Ser-Gln-Gln, extracted from green barley leaves, have been found to inhibit the adenosine diphosphate (ADP)-induced aggregation of human blood platelets.

6 Claims, 11 Drawing Sheets

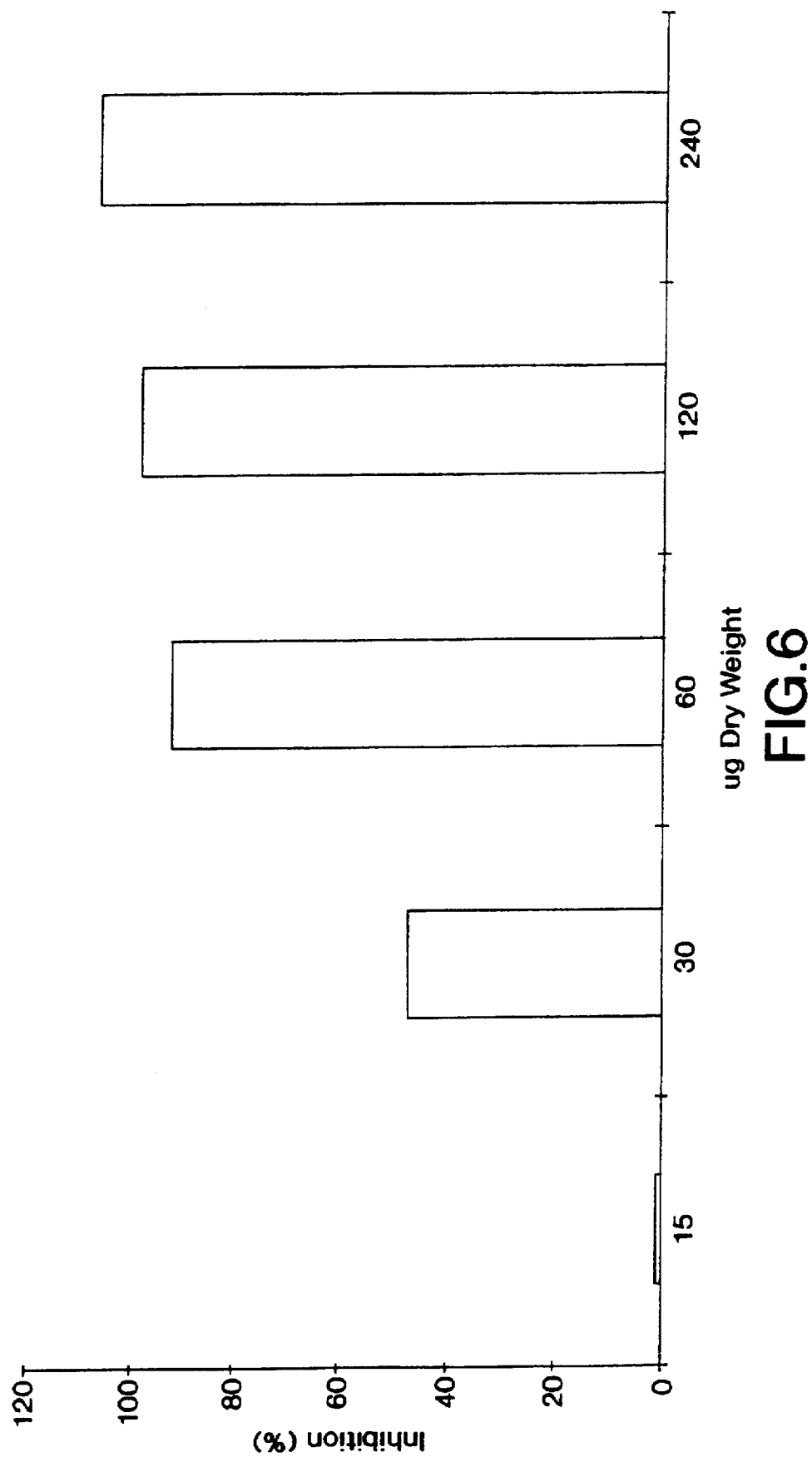

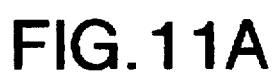
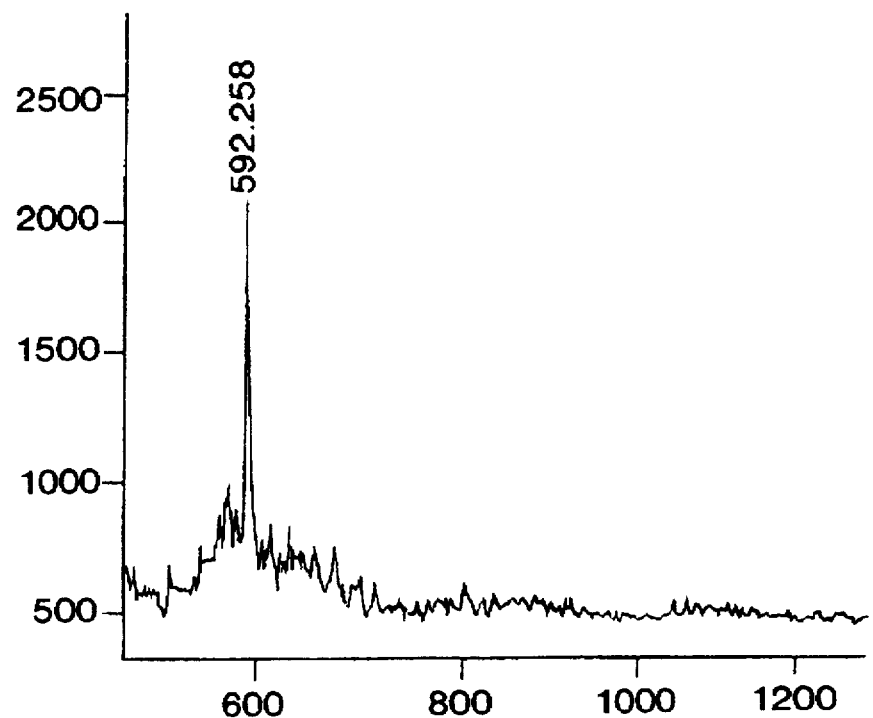
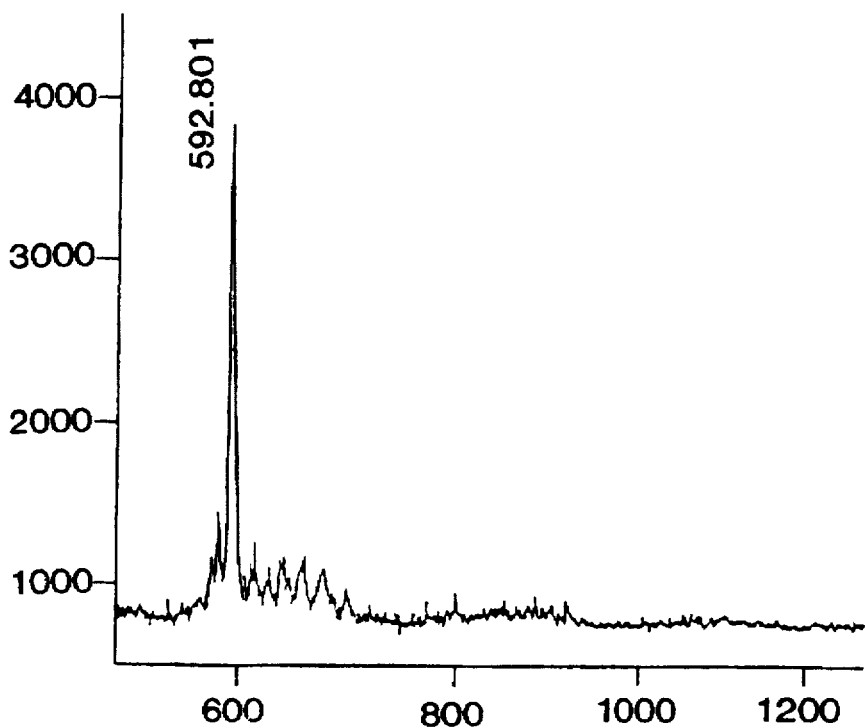

ISOLATION OF NOVEL PEPTIDES FROM GREEN BARLEY LEAF EXTRACT AND USE SAME TO INHIBIT HUMAN PLATELET AGGREGATION

BACKGROUND OF THE INVENTION

1. Field of the Invention

The present invention relates to the isolation and characterization of novel peptides obtained from a green barley leaf extract. More particularly, the present invention relates to the isolation and characterization of novel peptides, obtained from a green barley leaf extract, which inhibit human blood platelet aggregation.

2. Description of the Prior Art

Barley is used widely as a food stuff. The juice of young green barley leaves, and the lyophilisate thereof, is also widely used in Japan and other countries as a nutritional supplement. While being rich in vitamins and trace elements, extracts of the green leaves of young barley plants contain a complex mixture of largely undefined molecules with diverse alleged biological activities.

Recent studies have established that heated and unheated barley leaf extracts contain molecules that can enhance the release of growth hormone (GH) and prolactin beyond that achievable with GH releasing factor (GRF) or thyrotropin releasing hormone (TRH) alone. (GRF and TRH are the natural stimulators of growth hormone and prolactin, respectively.) [Badamchian, et al "Immune-Endocrine Activities Of Green Barley Leaf Extract (BLE): Regulation Of Prolactin And Interleukin-2 Release In Vitro" FASEB J. 5 A567 (1991).]

Young green barley leaves have been reported to contain biologically active substances such as antioxidants and anticarcinogens. A variety of immunomodulatory properties of green barley leaf extracts have also been reported to date, such as in vitro anti-inflammatory and anti-leukemic activity and reduced healing time of ulcerous lesions in rats. [Osawa, et al "A Novel Antioxidant Isolated From Young Green Barley Leaves", J. Agric. Food Chem., 40, 1135–1138 (1992); Itoh, et al "Study On the Anticancer Activity Of Green Juice Power Of Gramineae Plants", The 98th Annual Assembly of Pharmaceutical Society of Japan (1978); Kuhota, et al "Isolation Of Potent Anti-Inflammatory Protein From Barley Leaves", Japanese J. Inflam., 3, 4 (1983)]

Badamchian, et al "Isolation Of A Vitamin E Analog From A Green Barley Leaf Extract That Stimulates Release Of Prolactin And Growth Hormone From Rat Anterior Pituitary Cells In Vitro", J. Nutr. Biochem., 1994, Vol. 5, March, pp. 145–150, discloses α-tocopherol succinate as being the active element of green barley leaf extract that enhances the release of growth hormone and/or prolactin from rat anterior pituitary cells, in vitro. Reverse-phase high performance liquid chromatography (RP-HPLC) and fast atom bombardment-mass spectrometry (FAB-MS) were utilized to isolate and chemically characterize the α-tocopherol succinate molecule as the source of such neuroendocrine activity.

Badamchian, et al "α-Tocopherol Succinate, But Not α-Tocopherol Or Other Vitamin E Analogs, Stimulates Prolactin Release from Rat Anterior Pituitary Cells In Vitro", J. Nutr. Biochem., 1995, Vol. 6, June, pp. 1–5, discloses that only α-tocopherol succinate causes a significant increase in prolactin release from rat anterior pituitary cells, in vitro, but not other commercially available forms of α-tocopherol (e.g., α-tocopherol, δ-tocopherol, α-tocopherol acetate and α-tocopherol nicotinate) or succinic acid (e.g., succinic acid disodium salt and succinic acid (butanedioic acid)).

The present invention is based on continued efforts to assess the biological activity of the various molecules found in extracts from young green barley plants.

SUMMARY OF THE INVENTION

It is an object of the present invention to provide biologically active materials derived from barley plants.

In one embodiment, the present invention provides the novel penta-peptides Asp-Asp-Asn-Asp-Asn and Asp-Asp-Ser-Gln-Gln.

In another embodiment, the present invention provides a composition for the inhibition of blood platelet aggregation comprising the penta-peptide Asp-Asp-Asn-Asp-Asn and a pharmaceutically acceptable carrier therefor.

In a further embodiment, the present invention provides a composition for the inhibition of blood platelet aggregation comprising the penta-peptide Asp-Asp-Ser-Gln-Gln and a pharmaceutically acceptable carrier therefor.

In a yet further embodiment, the present invention provides a method for inhibiting blood platelet aggregation in a patient in need of such treatment comprising administering a blood platelet aggregation inhibitory effective amount of the pentapeptide Asp-Asp-Asn-Asp-Asn to said patient.

In a still yet further embodiment, the present invention provides a method for inhibiting blood platelet aggregation in a patient in need of such treatment comprising administering a blood platelet aggregation inhibitory effective amount of the penta-peptide Asp-Asp-Ser-Gln-Gln to said patient.

Other aspects of the invention will become clear upon review of the detailed description of the invention.

BRIEF DESCRIPTION OF THE DRAWING

Figures

FIG. 6 illustrates the dose dependent inhibition of ADP-induced platelet aggregation by fraction 13 (F13).

FIG. 11A illustrates a high resolution-fast atom bombardment-mass spectrograph of the peptide of fraction 13 (F13).

FIG. 11B illustrates a high resolution-fast atom bombardment-mass spectrograph of the peptide of fraction 14 (F14).

DETAILED DESCRIPTION OF THE INVENTION

Figure 1A:
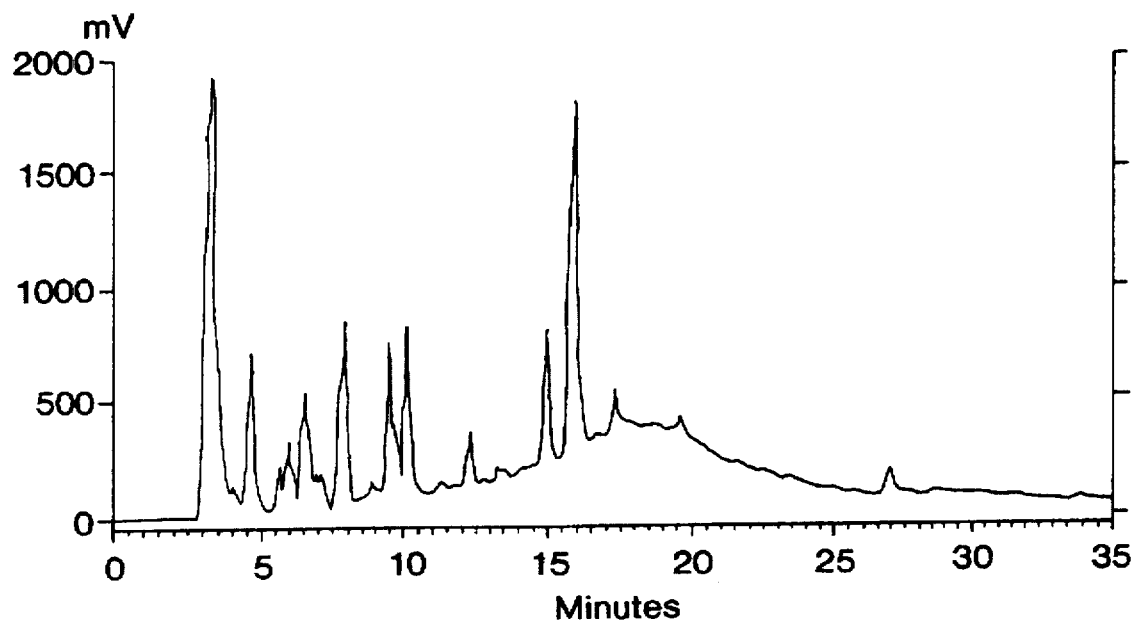
FIG. 1A is a reverse phase-high performance liquid chromatogram of Japanese barley leaf extract.

The present invention provides biologically active molecules derived from green barley plants.

The green leaves of barley plants are harvested shortly after germination, e.g., about 2 weeks. The leaves are lyophilized and subsequently ground to form a fine and uniform powder. (Typically, the powder will pass through a 2 mm mesh, although larger or smaller powder sizes can be utilized.)

The so-prepared powder is suspended in water (typically, using about 50 mg of powder per ml of $H_2O$) and stirred for a few minutes to a few hours at room temperature to about 100° C. (the higher the temperature the shorter the time necessary). Larger powder sizes or smaller relative amounts of powder may require relatively longer times and/or higher temperatures for efficient extraction of material from the powder.

The mixture can then be centrifuged and/or filtered to remove solid components therefrom. (If the extract so-produced is not to be used immediately, it may be stored at low temperature, e.g., 0° C., preferably −20° C.)

The so-produced extract can then be subjected to high performance liquid chromatography (i.e., reverse phase high performance liquid chromatography) so as to separate the extract into fractions of increasing hydrophobicity (e.g., eluent A may be an aqueous solution of trifluoracetic acid, eluent B may be an organic solvent (e.g., acetonitrile) solution of trifluoroacetic acid, and a linear gradient of from 0 to 80% B may be run). These fractions may be lyophilized, diluted with water, and assayed for biological activity (in the present case for the inhibition of adenosine diphosphate (ADP)-induced aggregation of blood platelets). Fractions exhibiting biological activity may be subjected to further reverse phase high performance liquid chromatography in order to further purify the active material.

Identification of the active material can then proceed by techniques well-known in their own right for qualitative and quantitative analysis.

Utilizing such techniques, two penta-peptides, Asp-Asp-Asn-Asp-Asn and Asp-Asp-Ser-Gln-Gln, have been isolated which inhibit ADP-induced aggregation of blood platelets, in vitro.

Based on the activity exhibited in these in vitro studies, it is believed that the administration of these penta-peptides, to a patient, in need of inhibition of blood platelet aggregation, in inhibitory effective amounts (e.g., 0.1–10 mg per kg of body weight) will effectively inhibit such blood platelet aggregation. Of course, the effective amount will vary with the age and overall health of the subject, as well as other factors.

Administration of the penta-peptides may be effected by direct injection or by utilization of an i.v. drip.

Pharmaceutically acceptable carriers for use with the pentapeptides include distilled water (sterile) and physiologically buffered saline (sterile), etc.

EXAMPLES

The following examples illustrate the preparation, separation and characterization of the novel peptides of this invention.

Extraction Procedure (i) Preparation Of Green Barley Leaf Powder

Green barley leaves were harvested two weeks after germination. The barley leaves were freeze-dried for 3 days in a freeze-dryer (Model 50-SRC-5 (Virtis Co., Gardner, N.Y., U.S.A.)). The freeze-dried leaves were subsequently ground with a Wiley mill Standard Model 3 (Arthur H. Thomas Co., Philadelphia, Pa. U.S.A.) equipped with a sieve (mesh size 2 mm) to form a fine and uniform powder for extraction.

(ii) Barley Leaf Extract (BLE)

Green barley leaf powder, prepared as above, was suspended in water (50 mg/ml) and stirred for one hour at room temperature. The mixture was then centrifuged at 3,000×g for 30 minutes using a bench-top centrifuge. The pellet was discarded and the supernatant was centrifuged at 30,000×g for 30 minutes. The supernatant was then centrifuged at 30,000×g for 30 minutes. It was then filtered through a 0.45 μm membrane (Millipore Corporation, Bedford, Mass.) and stored at −20° C. for high performance liquid chromatograph (HPLC) or biological assays.

(iii) Heated Barley Leaf Extract (H-BLE)

Green barley leaf powder, prepared as above, was suspended in water (50 mg/ml) and stirred for one hour at room temperature. The mixture was then centrifuged at 3,000×g for 30 minutes using a bench-top centrifuge. The pellet was discarded and the supernatant was centrifuged at 30,000×g for 30 minutes. The supernatant was then boiled for 10 minutes and then centrifuged at 30,000×g for 30 minutes. It was then filtered through a 0.45 μm membrane (Millipore Corporation, Bedford, Mass.) and stored at −20° C. for high performance liquid chromatography (HPLC) or biological assays.

High Performance Liquid Chromatography

Figure 1B:
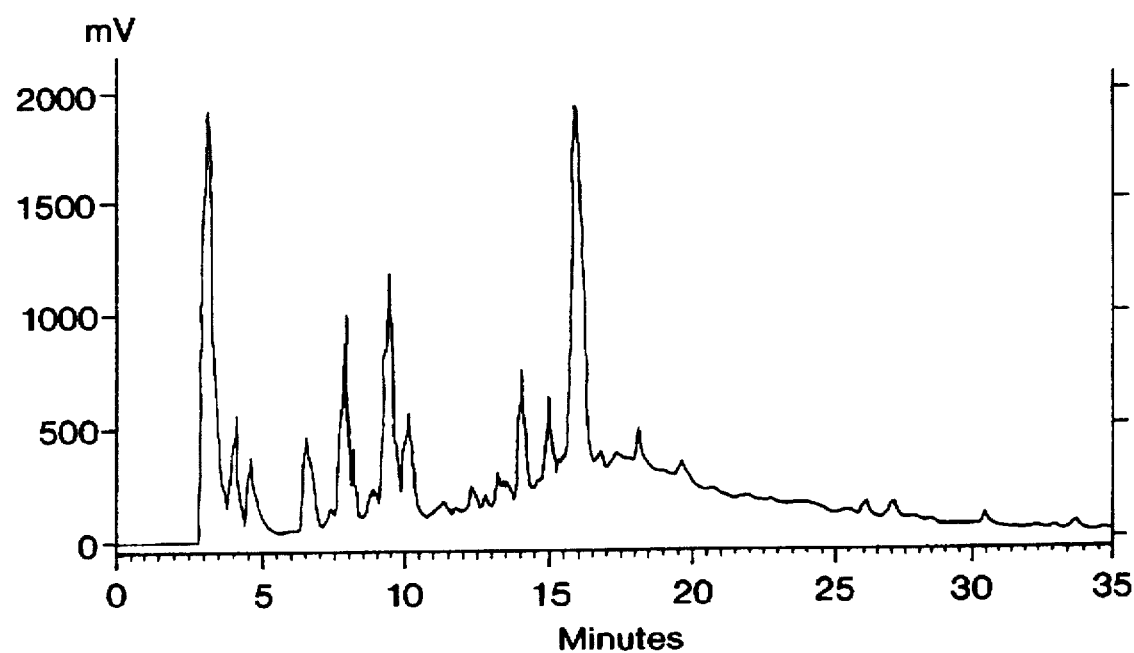
FIG. 1B is a reverse phase-high performance liquid chromatogram of Japanese heated barley leaf extract.

Optimization of reverse phase chromatography conditions for the fractionation of BLE or H-BLE was carried out on a Model 440 HPLC System (Waters, Milford, Mass. U.S.A.) equipped with a Model 490 multiwavelength detector set at 214 nm and 280 nm and a 300×3.9 mm Delta Pak 300 Å 15 μm $C_{18}$ column (Waters, Milford, Mass. U.S.A.). Eluent A was a 0.1% by weight aqueous solution of trifluoroacetic acid (TFA) and eluent B was acetonitrile containing 0.1% by weight TFA. A sixty minute linear gradient from 0 to 80% B was run at a flow rate of 1 ml/min. FIG. 1A shows reverse phase HPLC of BLE and FIG. 1B shows reverse phase HPLC of H-BLE.

Preparative reverse phase chromatography of H-BLE (300 mg) was performed on a Model 600 HPLC System (Waters), equipped with a Model 441 absorbance detector (Waters) set at 214 nm. and a 300×19 mm Delta Pak 300 Å, 15 μm C18 column. This was selected as the initial step for the fractionation of all peptides/molecules in BBLE or BLE. Eluent A was 0.1% by weight aqueous trifluoroacetate acid (TFA) and Eluent B was acetonitrile containing 0.1% by weight TFA. A sixty minute linear gradient from 0 to 80%

Figure 2:
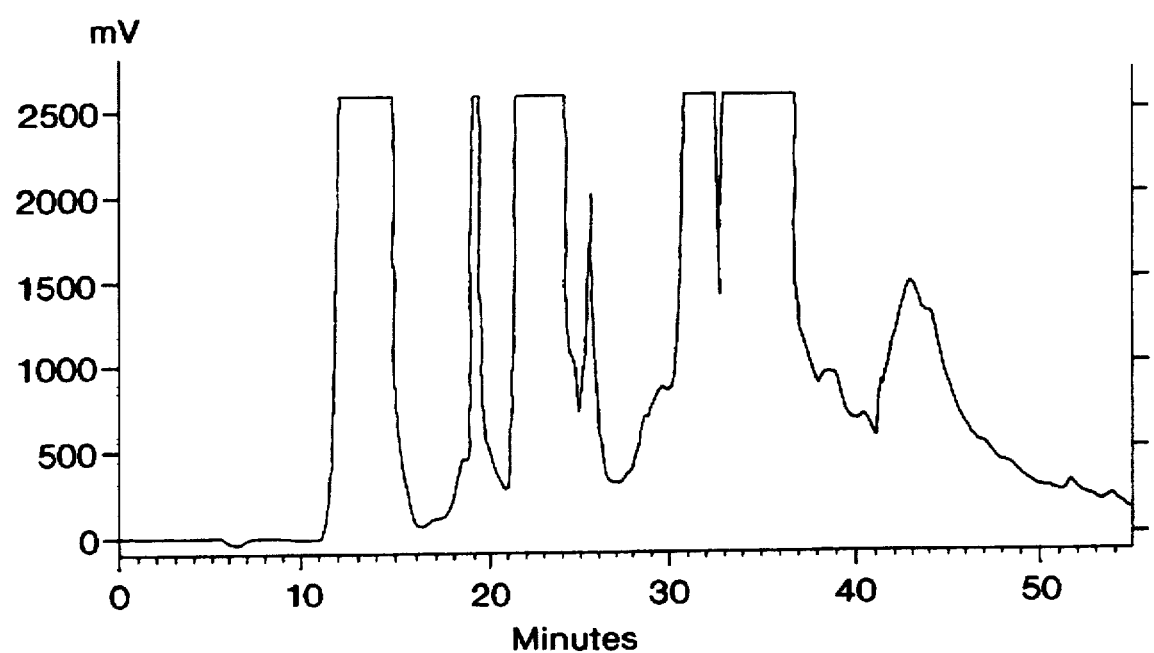
FIG. 2 is a reverse phase-high performance liquid chromatogram of the preparative separation of Japanese heated barley leaf extract.

B was run at a flow rate of 5 ml/min. FIG. 2 shows preparative reverse phase HPLC of H-BLE.

Figure 3:
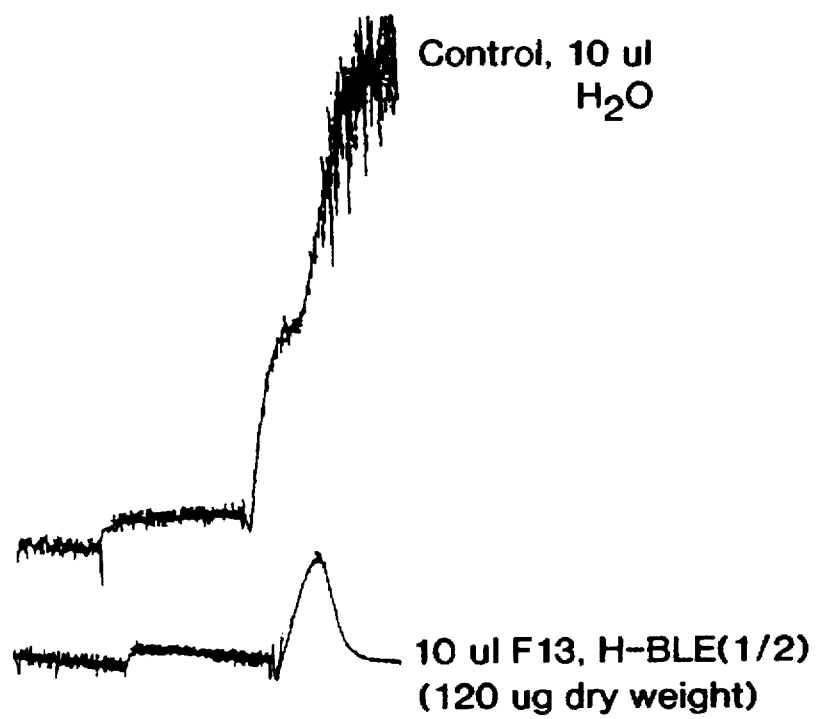
FIG. 3 illustrates the effect of fraction 13 (F13) on adenosine diphosphate (ADP)-induced platelet aggregation.
Figure 4:
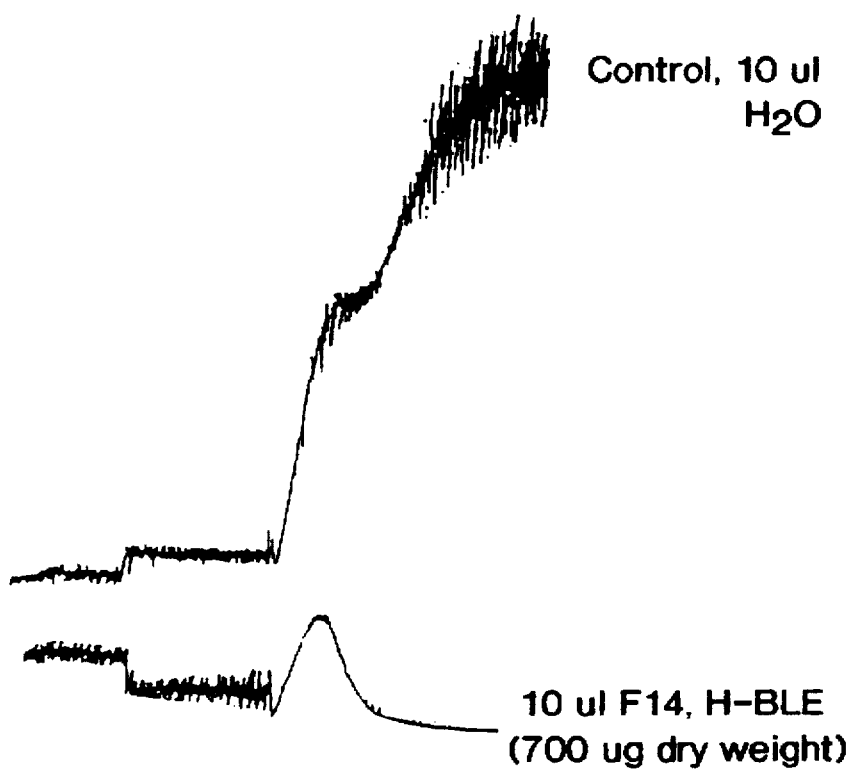
FIG. 4 illustrates the effect of fraction 14 (F14) on ADP-induced platelet aggregation.

One minute fractions were collected, lyophilized and diluted with 1 ml $H_2O$. The effect of each fraction on adenosine diphosphate (ADP)-induced platelet aggregation was tested. The results of this testing indicated that 10 μl of fraction 14 (F14) and fraction 13 (F13) had a significant inhibitory effect on ADP-induced platelet aggregation, see FIGS. 3 and 4. Therefore, F13 and F14 were subjected to further purification.

Figure 5A:
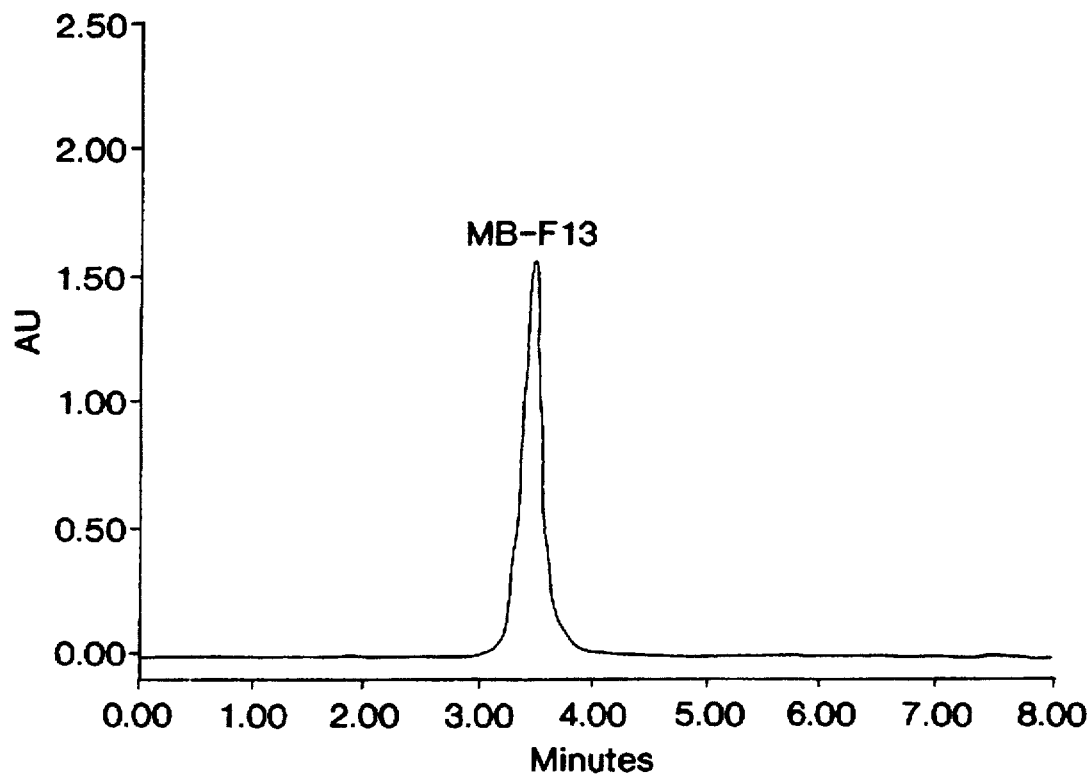
FIG. 5A is a reverse phase-high performance liquid chromatogram of fraction 13 (F13).
Figure 5B:
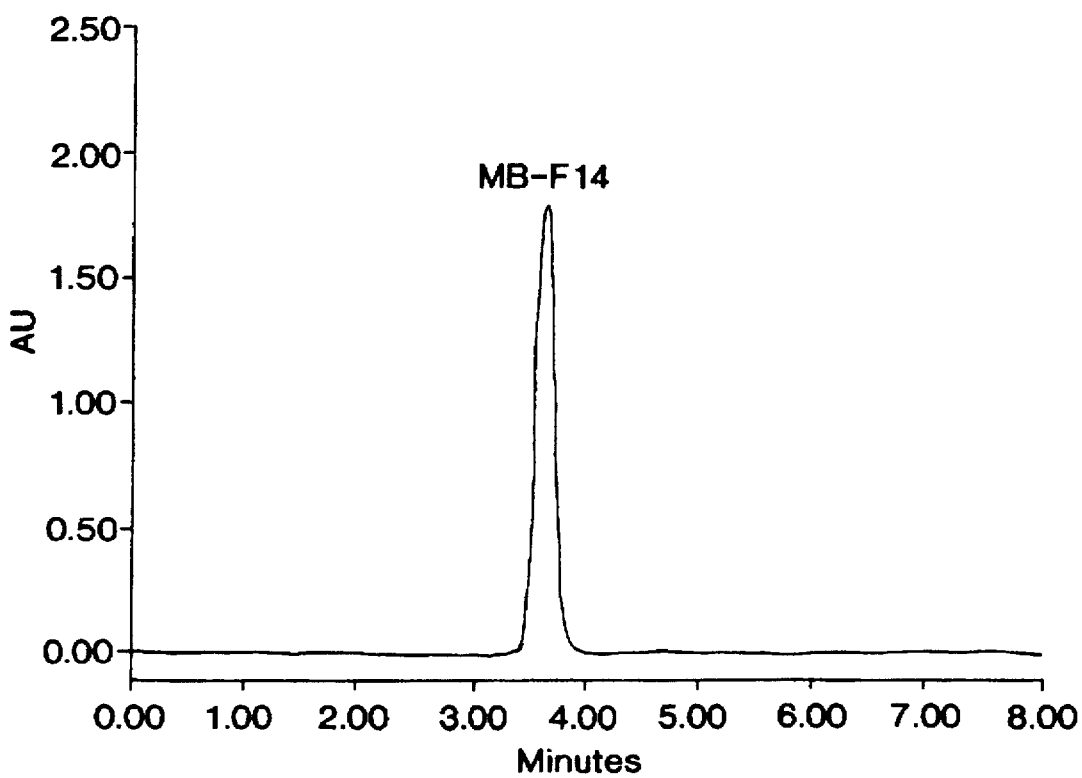
FIG. 5B is a reverse phase-high performance liquid chromatogram of fraction 14 (F14).
Figure 7:
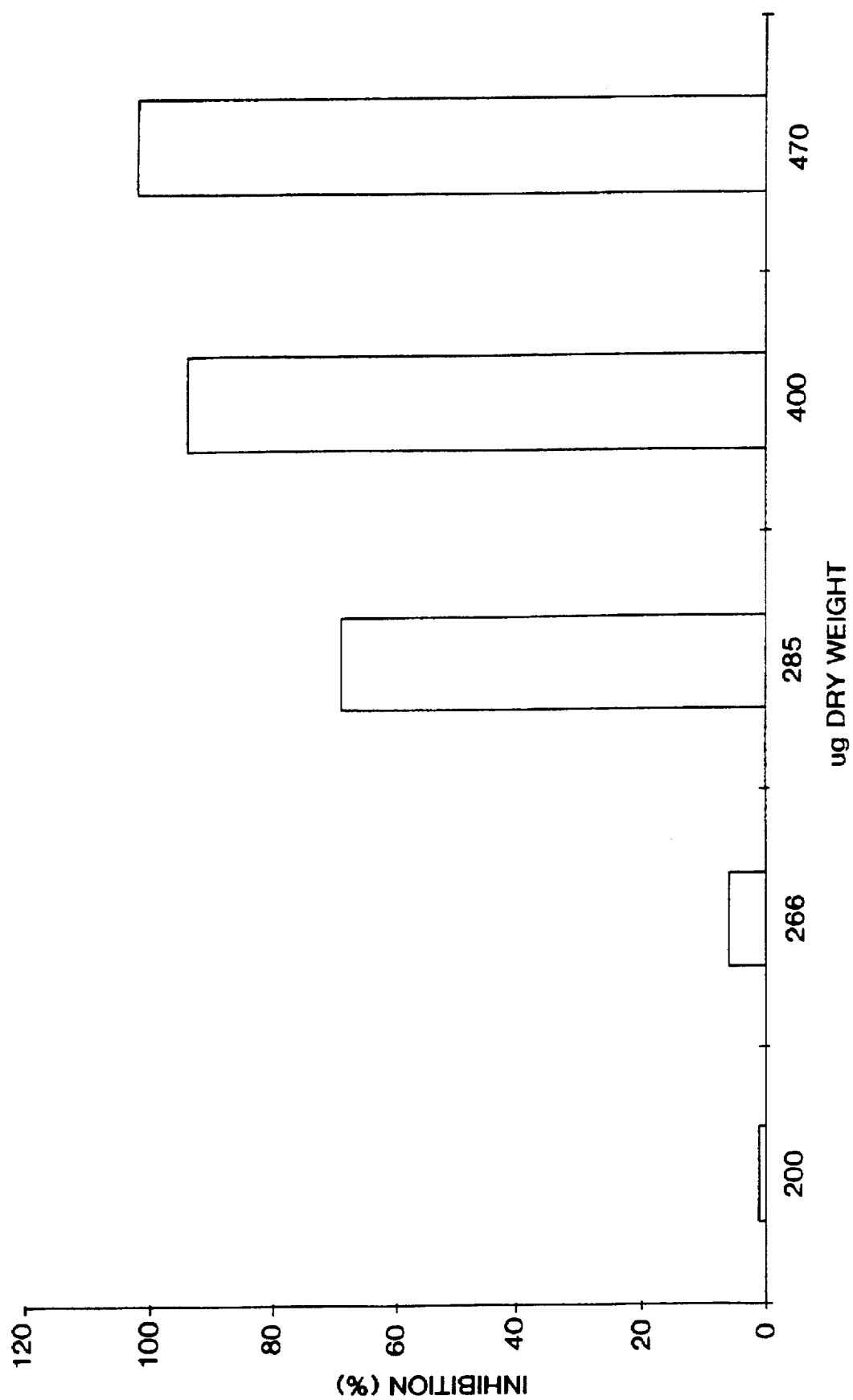
FIG. 7 illustrates the dose dependent inhibition of ADP-induced platelet aggregation by fraction 14 (F14).

Analytical reverse phase chromatograph of F13 and F14 was performed on a 3.9 mm×30 cm Delta Pak 300 Å, 5 μm, $C_{18}$ column. Eluent A was 0.1% by weight aqueous TFA and Eluent B was acetonitrile containing 0.1% by weight TFA. A 20 minute linear gradient from 0 to 5% B, followed by a five minute linear gradient from 5 to 20% B was run at a flow rate of 1 ml/min. Detection was at 214 and 218 nm. Half-minute fractions were collected and assayed for ADP-induced platelet aggregation. FIGS. 5A and 5B show the separation of fractions F13 and F14, respectively. Table 1 shows the recovery of peptide MB-F13 and peptide MB-F14 by protein concentration and dry weight. FIGS. 6 and 7 show the dose dependent inhibition of ADP-induced platelet aggregation by F13 and F14, respectively.

TABLE 1

Protein concentration and dry weight of peptides MB-F13 and MB-F14 generated from 1 gram H-BLE

| Sample | Dry weight (mg) | Protein | % yield (dry weight) |
|---|---|---|---|
| MB-F13 | 7.2 | 0.11 | 0.72 |
| MB-F14 | 141.0 | 8.33 | 14.1 |

Protein concentrations were measured by Lowry Protein assay using BSA as standard.

Platelet Aggregation Assay

For each experiment, 9 ml blood was collected, from a fasting, non-smoking, healthy subject, into a polypropylene tube containing 3.8% by weight sodium citrate using the two syringe technique. The samples were each diluted with 2 ml of phosphate-buffered saline. Platelet-rich plasma (PRP) was prepared by centrifuging the blood at room temperature for 3 minutes at 2000 RPM. After removal of the PRP, the sample was once again centrifuged for the preparation of platelet-poor plasma (PPP) for 10 minutes at 2700 RPM. With both PRP and PPP, the aggregometer was calibrated such that PRP gave zero and PPP produced 100% light transmission. Three controls were done in each experiment, one in the beginning, one in the middle, and one at the end. For each control, a 400 μl PRP sample was incubated with 4 μl of 1 μM $CaCl_2$ for 1 minute, and then with added water (an amount equivalent to the sample volume) for 2 minutes. Then 5-20 μl of 1–10 μM adenosine diphosphate (ADP) was added to the sample to obtain 100% aggregation.

Figure 8A:
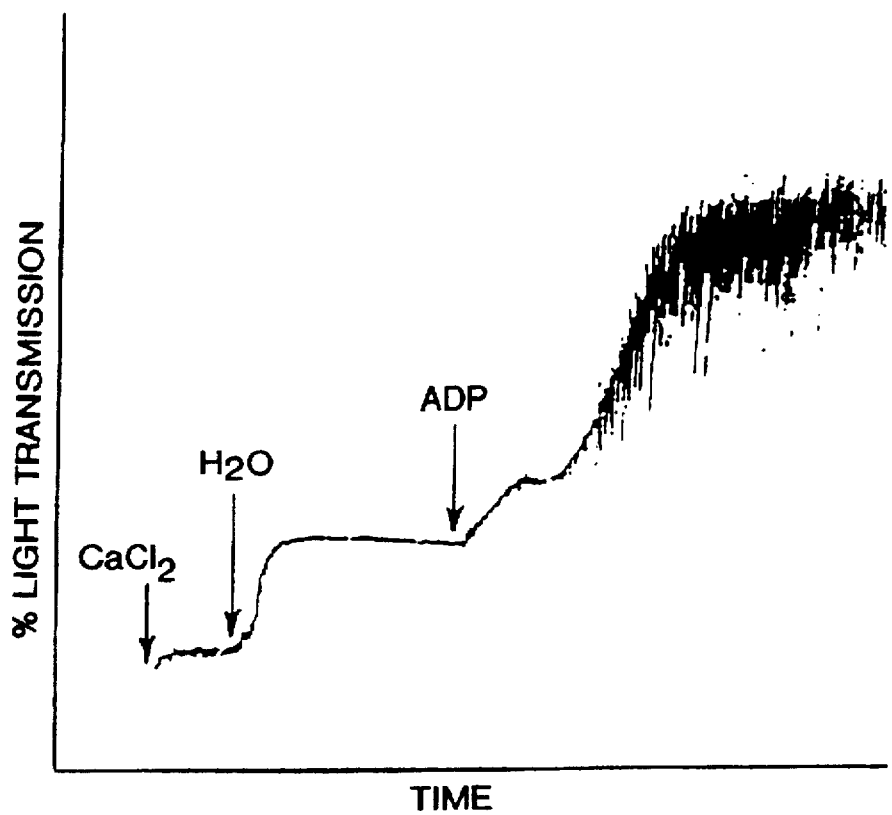
FIG. 8A illustrates ADP-induced platelet aggregation.
Figure 8B:
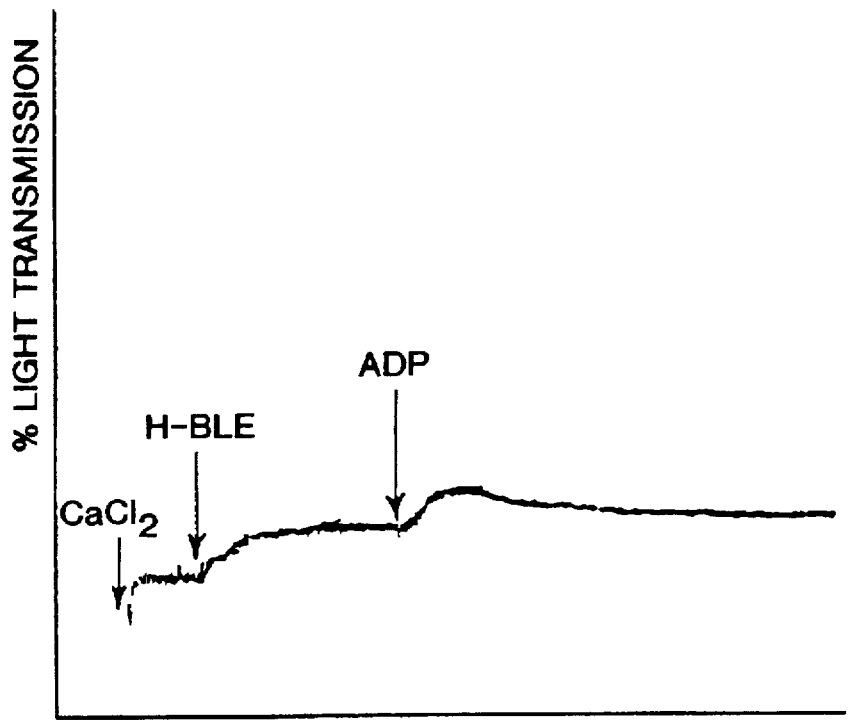
FIG. 8B illustrates the inhibition of ADP-induced platelet aggregation by heated-barley leaf extract (H-BLE).

FIG. 8A shows the effect of ADP (1μ mol) on inducing platelet aggregation of a control, as set forth above. Note the biphasic response (primary and secondary aggregation). FIG. 8B shows the effect of 40 μl (2 mg) of H-BLE on ADP-induced platelet aggregation.

Figure 9:
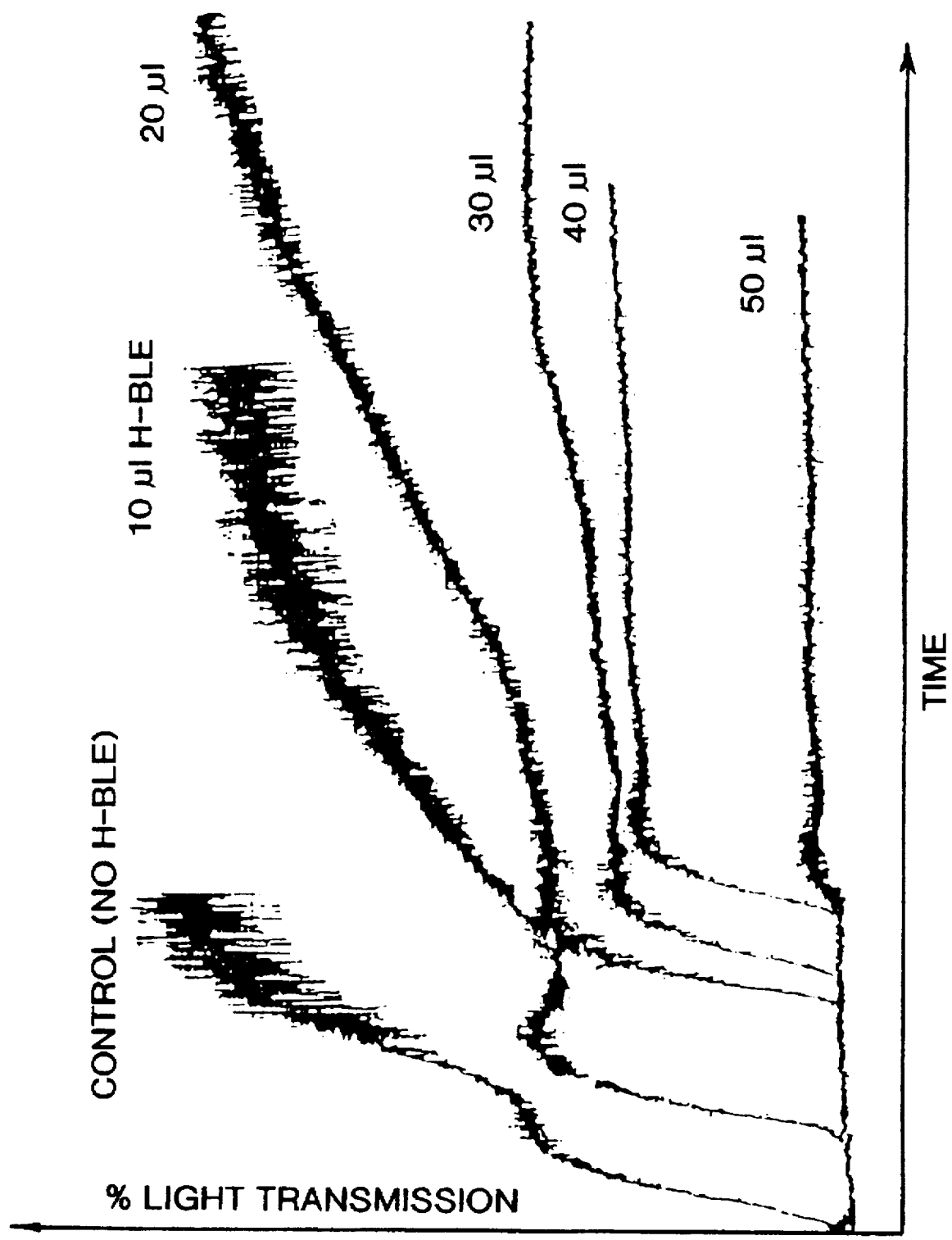
FIG. 9 illustrates the dose-dependent inhibition of ADP-induced platelet aggregation by heated-barley leaf extract (H-BLE).

FIG. 9 illustrates the dose-dependent inhibition of ADP-induced platelet aggregation by H-BLE.

The following TABLE 2 sets forth additional experiments with respect to the inhibition of ADP-induced platelet aggregation by various fractions of H-BLE containing varying concentrations of active components.

TABLE 2

| Exp. No. | Blood Plasma Source Sex | Age | 0.1M ADP added (μl) | H-BLE Fraction | Vol (μl) | Dry Wt. (μg) | Inhibition (%) |
|---|---|---|---|---|---|---|---|
| 1 | M | 17 | 8.2 | F13 | 10 | 240 | 106.0 |
| 2 | M | 17 | 8.2 | F13 | 10 | 120 | 98.0 |
| 3 | M | 17 | 8.2 | F13 | 10 | 60 | 92.0 |
| 4 | M | 17 | 8.2 | F13 | 10 | 30 | 47.0 |
| 5 | M | 17 | 8.2 | F13 | 10 | 15 | 0 |
| 6 | M | 17 | 8.2 | F14 | 10 | 940 | 108.0 |
| 7 | M | 17 | 8.2 | F14 | 10 | 470 | 102.0 |
| 8 | M | 17 | 8.2 | F14 | 10 | 235 | 3.0 |
| 9 | M | 17 | 8.2 | F14 | 10 | 118 | 1.0 |
| 10[1] | M | 17 | 8.2 | $H_2O$ | 10 | 0 | 0 |
| 11[1] | M | 17 | 8.8 | $H_2O$ | 10 | 0 | 0 |
| 12 | M | 17 | 8.8 | F14 | 10 | 700 | 104.0 |
| 13 | M | 17 | 8.8 | F14 | 10 | 400 | 94.0 |
| 14 | M | 17 | 8.8 | F14 | 10 | 285 | 69.0 |
| 15 | M | 17 | 8.8 | F14 | 10 | 266 | 6.0 |
| 16 | M | 17 | 8.8 | F14 | 10 | 200 | 0 |

Amino Acid Analysis (i) Composition

The amino acid analyses of peptides MB-F13 and MB-F14 were performed on a Pico-Tag Amino Acid Analysis System (Waters, Milford, Mass. U.S.A.). The method is based on the formation of phenylthiocarbamyl derivatives of the amino acids from acid-hydrolyzed proteins. In particular, samples of peptides MB-F13 and MB-F14 (1–5 μg) were hydrolyzed in 200 μl of constant boiling HCl containing 1% (vol/vol) phenol at 110° C. for 24, 48, 72 and 120 hours in the Pico-Tag work station. The hydrolysates were derivatized with phenylisothiocyanate for 20 minutes at room temperature to yield the corresponding phenylthiocarbamyl derivatives. These derivatives were analyzed with the Pico-Tag amino acid analysis system, which was previously calibrated with a standard mixture of amino acids. Table 3 shows the amino acid compositions of peptides MB-F13 and MB-F14.

TABLE 3

| Amino Acid [1] | Peptide MB-F13 | | Peptide MB-F14 | |
|---|---|---|---|---|
| | No. of residues from acid hydrolysis | No. of residues from the sequence | No. of residues from acid hydrolysis | No. of residues from the sequence |
| Asp[2] | 5 | 3 | 2 | 2 |
| Glu[2] | — | — | 2 | — |
| Ser | — | — | 1 | 1 |
| Asn | — | 2 | — | — |
| Gln | — | — | — | 2 |

[1]Calculated values for other amino acids were either zero or insignificant.
[2]Aspartic acid and glutamic acid values are the sum of their acids and amides.

(ii) Sequence

The amino acid sequence analysis of peptides MB-F13 and MB-F14 were performed on a Beckman LF 3400 Protein/Peptide Sequencer (Beckman Instruments, Inc., Fullerton, Calif., U.S.A.) All chemicals used for the automated Edman degradation were high sensitivity sequencing reagents consisting of: reduced concentration phenylisothiocyanate (PITC) (<1% PITC/Heptane); diisopropylethylamine (DIPEA) base; neat trifluoroacetic acid (TFA); ethyl acetate and DTT; 25% TFA/H$_2$O; PTH Amino Acid Standard (Pierce) 20 pmole/200 µl and acetonitrile/H$_2$O. The sequence data were obtained from the Beckman LF 3400 Protein/Peptide Sequencer with on-line HPLC equipped with a Beckman 126 gradient pump system, Beckman 168 Diode Array Detector, column heater, injector, System Gold software with protein sequencing software, and 2.1×15 cm 3 µm, Micro PTH column.

Peptides MB-F13 and MB-F14 were each composed of 5 amino acid residues and had the amino acid sequences as follows:

MB-F13: Asp-Asp-Asn-Asp-Asn
MB-F14: Asp-Asp-Ser-Gln-Gln

UV Spectrum

Figure 10A:
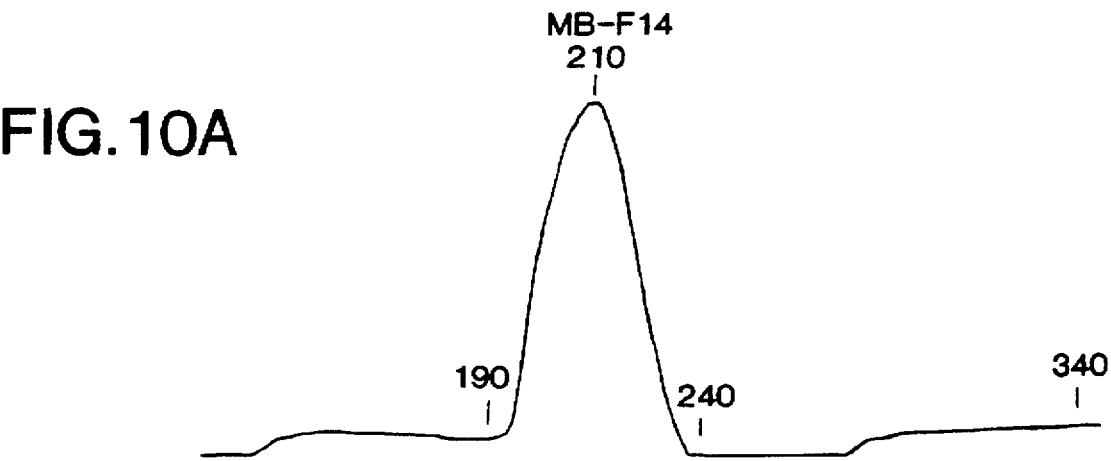
FIG. 10A illustrates the UV spectrum of the peptide of fraction 14 (F14).
Figure 10B:
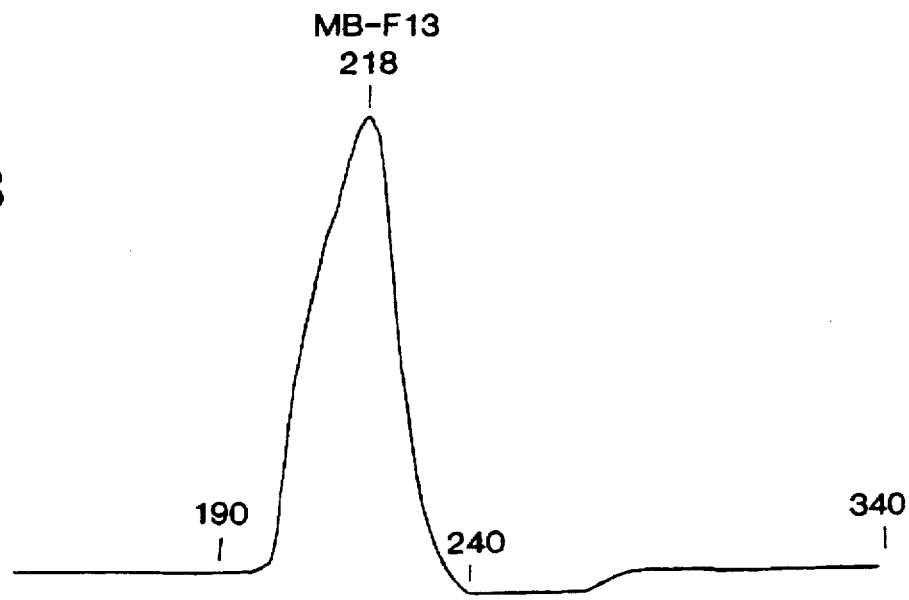
FIG. 10B illustrates the UV spectrum of the peptide of fraction 13 (F13).

FIG. 10A illustrates the UV spectrum of the peptide MB-F14 and FIG. 10B illustrates the UV spectrum of the peptide MB-F13. As may be readily ascertained, maximum absorbancy occurs at 210–218 nm and no absorbancy is exhibited at 260 nm. Absorbance at 210–218 nm is an indication of a peptide bond and no absorbance at 260 nm is an indication of the absence of an aromatic ring or an aromatic amino acid in the peptide.

Mass Spectrometric Analysis (i) Instrumentation

A linear time-of-flight mass spectrometer (TOF 101, Comstock, Inc., Oak Ridge, Tenn. U.S.A.) was modified to accommodate two laser ports, a viewport and high accelerating voltages up to 30 kV. The pressure was consistently lower than 10$^{-8}$ mbar in the ion source region. Above the probe tip, the 1 cm accelerating region was followed by a large diameter (7.13 cm) ion lens to maximize transmission. The interlocking design of lens elements eliminates field penetration and provides excellent field homogeneity. At the end of the 215 cm flight path, the ions were detected by a two state microchannel plate assembly, biased to −1800 V. Due to the relatively low mass of analyte ions, the accelerating voltage was kept at 10.00 kV throughout the study. Two high stability power supplies (Series 205B, Bertan Associates, Inc., Hicksville, N.Y.) provided ripple free operation even during high ion current operation.

The system was equipped with two laser sources: a nitrogen laser (VSL-337ND, Laser Science, inc., Newton, Mass. U.S.A.) emitting at a wavelength of 337 nm, and a dye laser (LPD 3000, Lambda Physik, Goettingen, Germany). The doubled output of the dye laser (Coumarin 540A dye) is tunable in the 275–290 nm range. A fast photodiode is used to measure the pulse width and monitor the proper operation of the lasers. Pulse energies are recorded by a pyroelectric joule meter. The nitrogen laser delivers up to 110 µJ in 5 ns FWHM pulses with maximum 5% shot-to-shot intensity fluctuations. Fluctuations in an average of 128 shots, however, were only around 1.4%. Thus, changes in fluctuations of the average intensity may carry information about the desorption process. The output of the doubled dye laser exceeds 400 µJ with 12 ns pulse width, when properly tuned. The laser irradiance was aajusted by a variable attenuator (935-5-OPT, Newport Corp., Fountain Valley, Calif. U.S.A.) and focused by a 254 mm focal length quartz lens onto the sample probe at 45°.

A 10x fast preamplifier (Model 9305, EG&G ORTEC, Oak Ridge, Tenn. U.S.A.) was followed by a variable gain amplifier module to extend the dynamic range of detection. After the two amplification states, the ion current was recorded by a fast transient digitizer (TR8828D, Lecroy, Albuquerque, N. Mex., U.S.A.). Data acquisition and analysis was performed on a 486D/33 MHz personal computer running custommade software (TOFWARE, Ilys Software, Pittsburgh, Pa. U.S.A.)

To provide uniform ionization conditions, the critical instrument parameters—accelerating voltage, laser irradiance, detector bias—were kept constant throughout the investigation. The laser irradiance was set to somewhat above the threshold for the poorest responding analyte and this value was kept consistent for all samples.

(ii) Sample Preparation

Tests were conducted using 3,5-dimethoxy-4-hydroxycinnamic acid (sinapinic acid, SA, Aldrich, Milwaukee, Wis.) and 2,5-dihydroxybenzoic acid (DHB Sigma, St. Louis, Mo.) as matrices. The DHB had to be recrystallized twice in order to remove excessive amounts of sodium salts present in the original product. Matrix solutions were prepared fresh every day in 7:3 (v/v) HPLC grade acetonitrile deionized water mixture. Analytes were purchased from Sigma (Sigma, St. Louis, Mo.)

Stock solutions of the peptides were prepared in 0.1% trifluoroacetic acid (TFA) to obtain 5×10$^{-4}$M concentrations. In the tests, 2 µl aliquots of the sample were mixed with 10 µl of matrix solution on the probetip (diameter 5 mm) leading to higher than 1000 matrix-to-sample ratios. (To test the effect of premixing, control experiments were performed, after vortex mixing in microcentrifuge tubes. The spontaneous mixing of matrix and sample, during the drying process, and vortex premixing led to identical results.) A stream of cold air was used to remove the solvent and produce an even distribution of crystals on the probetip.

(iii) Results

The mass spectrometric analysis of the penta peptides gave M+1 ion peaks at 592.3 and 592.8 for peptides MB-F13 and MB-F14, respectively. This data suggests that the molecular weights are 591.3 and 591.8. The calculated molecular weights from the amino acid composition and sequence analysis were 591.5 and 591.7 for penta peptides MB-F13 and MB-F14, respectively, FIG. 11A is a high resolution FAB-MS of peptide MB-F13. FIG. 11B is a high resolution FAB-MS of peptide MB-F14.

High Performance Capillary Electrophoresis

Figure 12A:
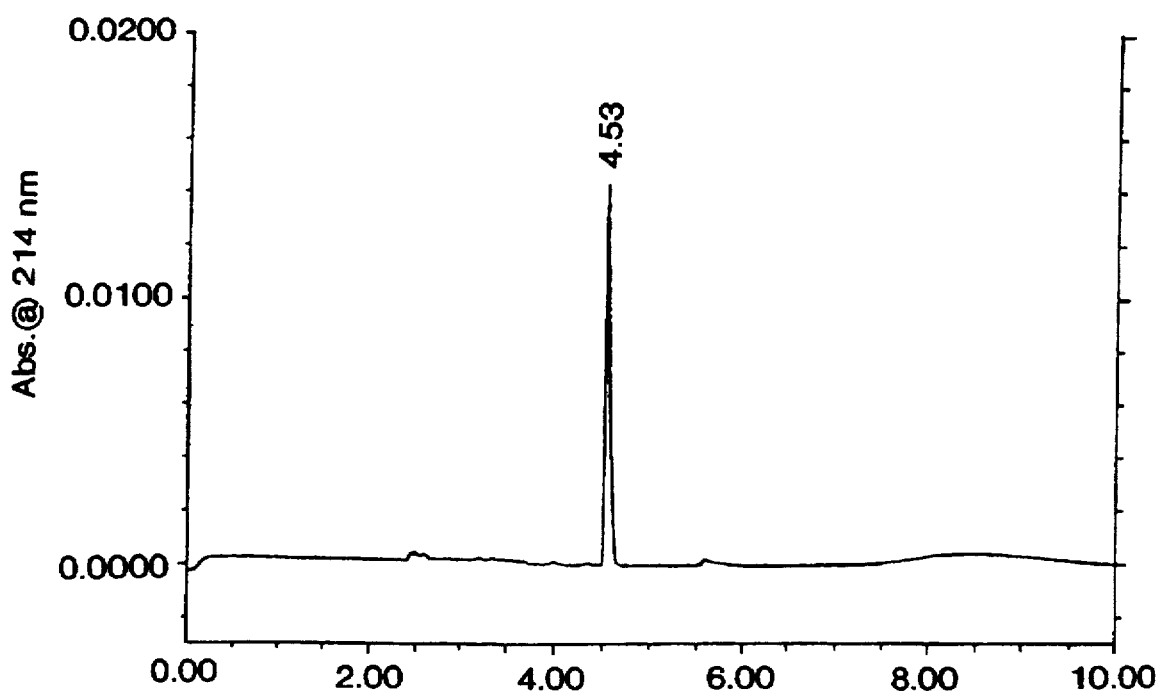
FIG. 12A illustrates the high performance capillary electrophoresis of the peptide of fraction 14 (F14).
Figure 12B:
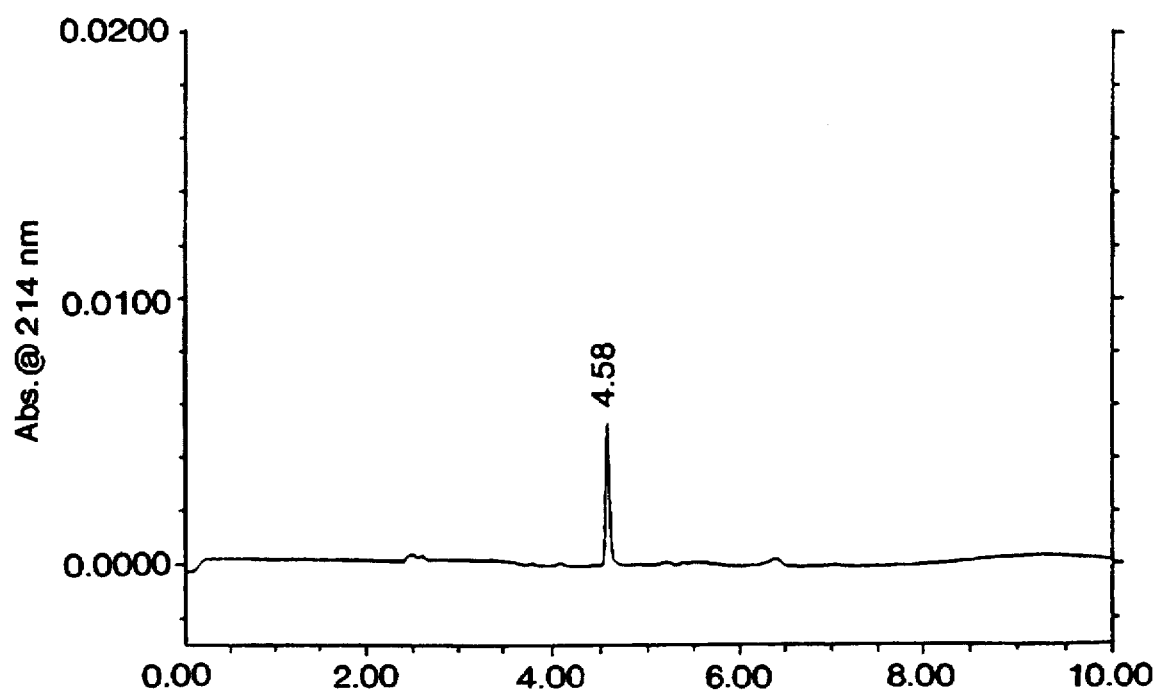
FIG. 12B illustrates the high performance capillary electrophoresis of the peptide of fraction 13 (F13).

High performance capillary electrophoresis was performed on a Beckman P/ACE System 5010. Separation of peptides MB-F13 and MB-F14 was performed in a 57 cm tube (50 cm to the detector) of 75 µm I.D. and 375 µm O.D., at room temperature, voltage of 20 Kv, buffer of 100 mM borate, pH 8.3 and detection at 214 nm. FIG. 12A is an electrophorogram for peptide MB-F14 and FIG. 12B is an electrophorogram for peptide MB-F13.

SEQUENCE LISTING

-continued

```
( 1 ) GENERAL INFORMATION:

( i i i ) NUMBER OF SEQUENCES:2

( 2 ) INFORMATION FOR SEQ ID NO: 1:

( i ) SEQUENCE CHARACTERISTICS:
            ( A ) LENGTH:5 amino acids
            ( B ) TYPE:amino acid
            ( C ) TOPOLOGY:linear ( i i ) MOLECULE TYPE:peptide ( v ) FRAGMENT TYPE:internal fragment ( i x ) FEATURE:
            ( A ) NAME/KEY:MB-F13
            ( B ) LOCATION:1-5
            ( C ) IDENTIFICATION METHOD:amino acid sequence analysis
            ( D ) OTHER INFORMATION:extracted from green leaves of barley
                  plants ( x ) PUBLICATION INFORMATION:
            ( K ) RELEVANT RESIDUES IN SEQ ID NO:from 1 to 5

( x i ) SEQUENCE DESCRIPTION:SEQ ID NO:1:

Asp  Asp  Asn  Asp  Asn
                                  5

( 2 ) INFORMATION FOR SEQ ID NO: 2:

( i ) SEQUENCE CHARACTERISTICS:
            ( A ) LENGTH:5 amino acids
            ( B ) TYPE:amino acid
            ( C ) TOPOLOGY:linear ( i i ) MOLECULE TYPE:peptide ( v ) FRAGMENT TYPE:internal fragment ( i x ) FEATURE:
            ( A ) NAME/KEY:MB-F14
            ( B ) LOCATION:1-5
            ( C ) IDENTIFICATION METHOD:amino acid sequence analysis
            ( D ) OTHER INFORMATION:extracted from green leaves of barley
                  plants ( x ) PUBLICATION INFORMATION:
            ( K ) RELEVANT RESIDUES IN SEQ ID NO:from 1 to 5

( x i ) SEQUENCE DESCRIPTION:SEQ ID NO:2:

Asp  Asp  Ser  Gln  Gln
                                  5
```

What is claimed is:

1. A composition consisting of the penta-peptide Asp-Asp-Asn-Asp-Asn.

2. A composition consisting of the penta-peptide Asp-Asp-Ser-Gln-Gln.

3. A composition for the inhibition of blood platelet aggregation consisting essentially of a blood platelet aggregation inhibitory effective amount of the composition according to claim 1 and a pharmaceutically acceptable carrier therefor.

4. A composition for the inhibition of blood platelet aggregation consisting essentially of a blood platelet aggregation inhibitory effective amount of the composition according to claim 2 and a pharmaceutically acceptable carrier therefor.

5. A method for inhibiting blood platelet aggregation in a mammal comprising administering a blood platelet aggregation inhibitory effective amount of the penta-peptide Asp-Asp-Asn-Asp-Asn to said mammal.

6. A method for inhibiting blood platelet aggregation in a mammal comprising administering a blood platelet aggregation inhibitory effective amount of the penta-peptide Asp-Asp-Ser-Gln-Gln to said mammal.

* * * * *